United States Patent [19]
Taylor et al.

[11] Patent Number: 6,066,732
[45] Date of Patent: May 23, 2000

[54] PROCESS FOR THE PREPARATION OF PYRROLO[2,3-D]PYRIMIDINES

[75] Inventors: Edward C. Taylor, Princeton; Bin Liu, Plainsboro, both of N.J.

[73] Assignee: The Trustees of Princeton University, Princeton, N.J.

[21] Appl. No.: 09/138,354

[22] Filed: Aug. 21, 1998

[51] Int. Cl.⁷ .................... C07D 487/04; C07D 239/47; C07D 239/48

[52] U.S. Cl. .................... 544/280; 544/317; 544/319

[58] Field of Search .................... 544/280, 317, 544/319

[56] References Cited

FOREIGN PATENT DOCUMENTS 0334636  3/1989  European Pat. Off.

OTHER PUBLICATIONS

Bartlett, P.A.; Green. F..R.; Webb, T.R., "t–BuOOH and t–BuOK with a catalyst [VO(acac)₂]", *Tetrahedron Lett.* 1977, 331.

Barton, D.H.R.; Motherwell, W.B.; Zard, S.Z. Tetrahedron Lett., 1983, 24, 5227; Schechter, H.; Williams, F.T. Jr. *J. Org. Chem.*, 1962, 27, 3699; Freeman, F.; Yeramyan, A.*J. Org. Chem.*, 1970, 35, 2061; Freeman, F.; "Use of KmnO₄".

Keinan, E.; Mazur, Y.J., "Activated dry silica gel", Am. Chem. Soc. 1977, 99, 3861.

Lin, D.K. *J. Org. Chem.*, 1971, 36, 1335; Kornblum, N.; Erickson, A.S.; Kelly, W.J.; Henggeler, B.*J. Org. Chem.*, 1982, 47, 4534; Steliou, K.; Poupart, M.A. *J. Org. Chem.* 1985, 50, 4971.

McMurry, J.E.; Melton, J.; Padgett, H., "Use of ozone", *J. Org. Chem.*, 1974, 39, 259.

McMurry, J.E.; Melton, J., "Aqueous TiCl₃", *J. Org. Chem.* 1973, 38, 4367; McMurry, J.E. *Acc. Chem. Res.* 1974, 7, 281.

Olah, G. A.; Arvanaghi, M.; Vankar, Y.D.; Prakash, G.K.S., "H₂O₂/K₂CO₃", *Synthesis* 1980.

Olah, G.A.; Gupta, B.G. B., "Use of ceric ammonium nitrate (CAN)", *Synthesis*, 1989, 44.

Pinnick, H.W., "Review of the Nef reaction", *Org. React.* 1990, 38, 655.

Urpi, F.; Vilarrasa, J. "Tin complexes and NaHSO₃ (SnCl₂–H₂O,PhSH, tartaric acid and NaHSO₃))" *Tetrahedron Lett.* 1990, 31, 7499.

Vankar, D.S.; Rathore, R.; Chandrasckaran, S., "Use of cetyltrimethylammonium permanganate", *Synth. Commun.* 1987, 17, 195.

*Primary Examiner*—John M. Ford
*Attorney, Agent, or Firm*—Mathews, Collins, Shepherd & Gould, P.A.

[57] ABSTRACT

4(3H)-X-7H-Pyrrolo[2,3-d]pyrimidines in which X is =O or =NH are prepared by treating a 6-amino-4(3H)-X-pyrimidine with a unsubstituted or substituted 1-nitroalk-1-ene to yield a 6-amino-4(3H)-X-pyrimidine which is substituted in the 5-position by a 1-nitroalk-2-yl group; (ii) converting the 5-(1-nitroalk-2-yl)-6-amino-4(3H)-X-pyrimidine to the corresponding 5-(1-oxoalk-2-yl)-6-amino-4(3H)-X-pyr-imidine; and (iii) removing the elements of water from the 5-(1-oxoalk-2-yl)-6-amino-4(3H)-X-pyrimidine to effect cyclization. A typical embodiment involves treating 2,6-diamino-4(3H)-pyrimidone with 1-nitro-4-(4-ethoxycarbonylphenyl)-1-butene to yield 1-nitro-2-(2,6-diamino-4(3H)-oxopyrimidin-5-yl)-4-(4-ethoxy-carbonylphenyl)butane which is then treated sequentially with base and acid, without isolation of the intermediate aldehyde, to form 4-[2-(2-amino-4(3H)-oxo-7H-pyrrolo[2,3-d]pyrimidin-5-yl)ethyl]benzoic acid, a valuable known chemical intermediate for the preparation of N-[4-{2-(2-hydroxy-4-amino-7H-pyrrolo[2,3-d]-pyrimidin-5-yl)ethyl}benzoyl]glutamic acid.

29 Claims, No Drawings

PROCESS FOR THE PREPARATION OF PYRROLO[2,3-D]PYRIMIDINES

BACKGROUND OF THE INVENTION

This invention pertains to a process for the preparation of compounds containing the fused heterocyclic pyrrolo[2,3-d]pyrimidine ring system which can be depicted as follows:

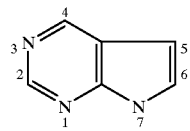

A variety of compounds containing this ring system have been described in the literature. 7-Deazaguanine is a pyrrolo[2,3-d]pyrimidine reported by Davoll, *J. Chem. Soc.,* 1960, 131. The pyrrolo[2,3-d]pyrimidine ring also is found in queuine, the aglycon of queuosine, and in the N-[4-{3-(2,4-diamino-7H-pyrrolo[2,3-d]pyrimidin-5-yl)propyl}benzoyl]glutamic acid derivatives described in U.S. Pat. No. 4,997,838. 5-Aminoalkynylpyrrolo[2,3-d]pyrimidines are described in U.S. Pat. No. 5,047,519. Fluorescent dyes containing the pyrrolo[2,3-d]pyrimidine ring system are used as reagents to identify guanosine and adenosine terminators in the automated sequencing of DNA {See Cocuzza, *Tetrahedron Left.,* 29, No. 33, 4061}. U.S. Pat. No. 5,344,932 describes N-[4-{2-(2-hydroxy-4-amino-7H-pyrrolo[2,3-d]pyrimidin-5-yl)ethyl}benzoyl]glutamic acid and related compounds as being antineoplastic agents (See also, Taylor et al., *J. Med. Chem.,* 1992, 35, 4450). U.S. Pat. Nos. 4,996,206, 5,028,608, and 5,248,775 describe other antineoplastic agents which also have the pyrrolo[2,3-d]pyrimidine ring system.

Typically in these compounds, the 2-position of the pyrrolo[2,3-d]pyrimidine ring will be unsubstituted or substituted with amino, but alternatively can carry an unsubstituted or substituted group such as alkyl, aralkyl, aryl, alkylthio, aralkylthio, or arylthio. The 4-position of the pyrrolo[2,3-d]pyrimidine ring generally will carry an oxo or amino group. (It will be appreciated that the 4(3H)-oxopyrrolo[2,3-d]pyrimidine and 4(3H)-iminopyrrolo[2,3-d]pyrimidine structures are the tautomeric equivalents of the 4-hydroxypyrrolo[2,3-d]pyrimidine and 4-aminopyrrolo[2,3-d]pyrimidine structures, respectively). The principal points of structural variation generally involve the 5- and 7-positions of the pyrrolo[2,3-d]pyrimidine structure, that is, the second carbon atom from the ring nitrogen atom of the pyrrole ring and the ring nitrogen atom itself of the pyrrole ring, respectively.

Substitution of the nitrogen atom in the 7-position generally does not pose a serious problem. Introducing a substituent in the 5-position, however, is considerably more problematical. One synthetic approach involves synthesizing the pyrrolo[2,3-d]pyrimidine system and then coupling this, typically as a 5-halo derivative, with a reagent carrying a precursor for the substituent in the 5-position. See e.g. Cocuzza, supra, and U.S. Pat. No. 5,344,932. This route requires synthesis of the 5-substituted pyrrolo[2,3-d]pyrimidine intermediates, which often is difficult, as well as the performance of a number of synthetic steps subsequent to coupling.

An alternative approach involves constructing the pyrrolo[2,3-d]pyrimidine ring through cyclization, as for example, allowing an α-dicyanomethyl derivative of a substituted alkanoic acid ester to react with guanidine. See e.g. U.S. Pat. No. 4,997,838.

Yet a further approach involves the reaction of a nucleophile of the formula $R^2-C(=NH)NH_2$ and a 2-amino-5-substituted-furan carrying a cyano or carboxy group in the 4-position, as described for example in U.S. Pat. No. 5,254,687, Taylor et al., *J. Org. Chem.,* 60, 6684 (1995), and Taylor et al., *J. Org. Chem,* 61, 7973 (1996). For example ethyl 4{2-(2,4-diaminopyrrolo[2,3-d]pyrimidin-5-yl)-ethyl}benzoate, an intermediate for the preparation of the known N-[4-{2-(2,4-diaminopyrrolo[2,3-d]pyrimidin-5-yl)ethyl}benzoyl]-L-glutamic acid, is prepared by allowing guanidine and ethyl 4-[2-(2-amino-3-cyanofur-4-yl)ethyl]benzoate to react under mild conditions. The known N-[4-{3-(2,4-diaminopyrrolo[2,3-d]pyrimidin-5-yl)propyl}benzoyl]-L-glutamic acid is similarly prepared from methyl 4-[3-(2-amino-3-cyanofur-4-yl)propyl]benzoate.

The present invention involves a new process for preparing pyrrolo[2,3-d]pyrimidine compounds that is direct, inexpensive, and capable of broad applicability. The process permits synthesis of a wide variety of 7H-pyrrolo[2,3-d]pyrimidines, including but not limited to those described in U.S. Pat. Nos. 5,344,932, 5,254,687, 4,996,206, 5,028,608, and 5,248,775, that are substituted in the 5-position. In the present process, the 5-substituent (designated herein as "R") is "pendant" and not involved in any way in the formation of the bicyclic structure so that it can be varied widely in carbon content and structure.

DETAILED DESCRIPTION

According to a first aspect of the present invention, a 6-amino-5-(1-R-2-nitroethyl)pyrimidine of Formula I is converted to the corresponding 7H-pyrrolo[2,3-d]pyrimidine substituted with R in the 5-position, as shown in Formula II:

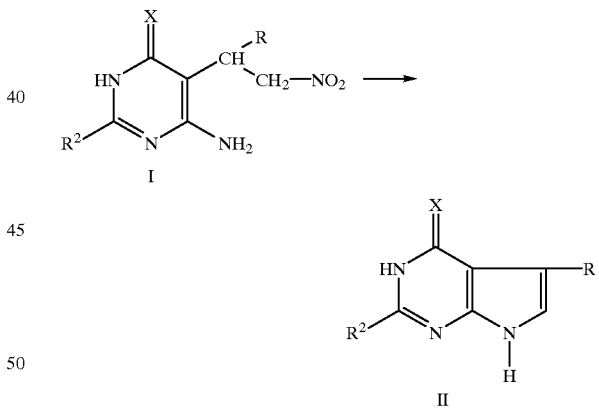

In this reaction, X is =O or =NH. R can be virtually any group which is stable to mild base and acid, including for example any of the nucleophile-stable substituents described in U.S. Pat. No. 5,254,687. R can be hydrogen or an unsubstituted or substituted alkyl, aralkyl, aryl, or heterocyclic group which itself can be unsubstituted or substituted. The substitution can include protecting groups, utilized in one or more earlier reactions, which can be removed in the course of the cyclization reaction. For example R in Formula I may include a carbalkoxy group which in the course of the reaction may be advantageously converted to a free carboxylic acid group.

$R^2$ also is not involved in the transformation and can be any of the groups described in U.S. Pat. No. 5,254,687 in the 2-position; e.g., hydrogen, amino, or an unsubstituted or substituted alkyl, aralkyl, aryl, alkylthio, aralkylthio, or arylthio group.

While not wishing to be bound by any theory, it is believed the transformation of a compound of Formula I to a compound of Formula II involves several steps, analogous to those thought to occur in the classical Nef reaction. In particular, it is believed that the nitro group in compound I is first converted to an aldehyde of Formula IA:

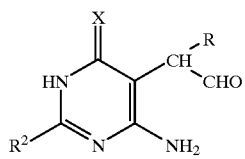

IA

The aldehyde in turn cyclizes and loses the elements of water. Significantly, however, all these conversions can be accomplished in a "one pot" environment while achieving overall yields from Formula I to Formula II that are greater than 55%.

The reactions are straightforward, requiring no special equipment nor critical reaction conditions. The nitro compound can be converted to the corresponding aldehyde through a variety of techniques, as for example, the use of cetyltrimethylammonium permanganate, see e.g., Vankar et al., *Synth. Commun.* 1987, 17, 195; the use of hydrogen peroxide and potassium carbonate, see, e.g., Olah et al, *Synthesis* 1980; various tin complexes and sodium bisulfite, see, e.g., Urpi et al. *Tetrahedron Left.* 1990, 31, 7499; the use of potassium permanganate, see, e.g., Barton et al., *Tetrahedron Lett.*, 1983, 24, 5227; Schechter et al.,*J. Org. Chem.*, 1962, 27, 3699; Freeman et al., *J. Org. Chem.*, 1970, 35, 2061; Freeman et al., *J. Org. Chem.*, 1971, 36, 1335; Kornblum et al.,*J. Org. Chem.*, 1982, 47,4534; and Steliou et al., *J. Org. Chem.* 1985, 50, 4971; the use of aqueous titanium chloride, see e.g., McMurry et al., *J. Org. Chem.* 1973, 38, 4367 and McMurry,*Acc. Chem. Res.* 1974, 7, 281; the use of ceric ammonium nitrate, see, e.g., Olah, et al., *Synthesis,* 1989, 44, the use of tert.-butyl peroxide and tert.-butoxide, see e.g., Bartlett et al, *Tetrahedron Lett.* 1977, 331; and the use of ozone, see e.g., McMurry et al., *J. Org. Chem.*, 1974, 39, 259. For a general review, see Pinnick, *Org. React.* 1990, 38, 655. Similarly, removal of the elements of water from the putative aldehyde can be achieved through any of the conventional dehydration techniques.

In a particularly elegant method, a compound of Formula I is simply stirred in aqueous base at ambient temperatures for several hours followed by addition to aqueous acid such as sulfuric acid at reduced temperatures; e.g., ~0° C., for several hours to remove the elements of water and effect cyclization. The pH is adjusted to essentially neutrality and the mixture stirred briefly at room temperature. Upon acidification, the product is collected and further purified by conventional methods such as recrystallization or chromatography.

Protecting groups denote radicals which generally are not found in the final compounds but which are intentionally introduced at a stage of the synthesis in order to protect groups which otherwise might react in the course of chemical manipulations, thereafter being removed at a later stage of the synthesis. Since compounds bearing such protecting groups thus are of importance primarily as chemical intermediates, their precise structure is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, N.Y., 1981; "The Peptides", Vol. I, Schroder and Lubke, Academic Press, London and New York, 1965; "Methoden der organischen Chemie", Houben-Weyl, 4th Edition, Vol.15/1, Georg Thieme Verlag, Stuttgart 1974.

Solely by reason of the groups predominantly found in the final compounds, $R^2$ in the first reactant generally will be hydrogen or amino. $R^2$ can, however, be a variety of other groups such as an unsubstituted or substituted alkyl, aralkyl, aryl, alkylthio, aralkylthio, or arylthio group. Typically the alkyl portion of these groups will contain 1 to 6 carbon atoms and the aryl groups will be an unsubstituted or substituted phenyl or naphthyl group.

In a preferred embodiment, the 6-amino-5-(1-R-2-nitroethyl)-4(3H)-X-pyrimidine of Formula I is a 2,6-diamino-4(3H)-X-pyrimidine in which R is a 1-nitrobut-2-yl or 1-nitropent-2-yl group further substituted with a cyclic structure:

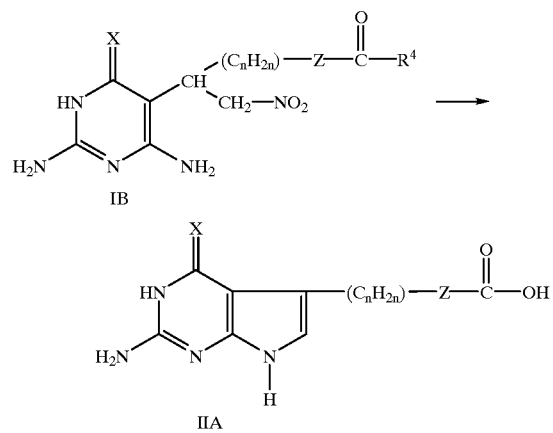

In the foregoing, X is as defined above, $R^4$ is a carboxylic acid protecting group, Z is phenylene, thienediyl, or furandiyl, and n has a value of 0 to 4, notably 2 or 3. Z preferably is 1,3-phenylene, 1,4-phenylene, thiene-2,4-diyl, thiene-2,5-diyl, thiene-3,4-diyl, or thiene-3,5-diyl, most preferably 1,4-phenylene.

By allowing a compound of Formula IIA or a reactive derivative thereof to react with a protected glutamic acid derivative under known amide forming conditions, a variety of previously described pharmaceutical agents such as N-[4-{2-(2-amino-4-hydroxypyrrolo[2,3-d]pyrimidin-5-yl) ethyl}benzoyl]-L-glutamic acid and N-[4-{3-(2,4-diaminopyrrolo[2,3-d]pyrimidin-5-yl)propyl}benzoyl] glutamic acid can be readily prepared; See, e.g., U.S. Pat. Nos. 5,344,932, 4,996,206, 5,028,608, 5,248,775, and 4,997,838.

Alternatively, the group $R^4$ is —NHCH(COOH)CH$_2$CH$_2$COOH or a protected derivative thereof, leading directly, upon treatment of the compounds of Formula IB according to the present process, to the glutamic acid derivatives of U.S. Pat. Nos. 5,344,932, 4,996,206, 5,028, 608, 5,248,775, and 4,997,838

According to a further aspect of the present invention, the 2,6-diamino-5-(1-R-2-nitroethyl)-4(3H)-X-pyrimidine of Formula I utilized above is obtained by allowing a 6-amino- 4(3H)-X-pyrimidine of Formula III to react with 1-R-2-nitroolefin of Formula IV:

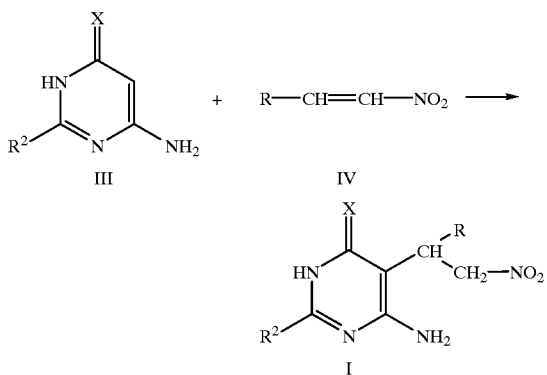

This reaction, which is analogous to a Michael addition with the 6-amino-4(3H)-X-pyrimidine constituting the Michael donor and the nitroolefin of Formula IV constituting the Michael acceptor, is effected simply by stirring the two reactants at ambient temperatures, as for example 20 to 30° C., in an inert aqueous solvent such as aqueous ethyl acetate. The reaction proceeds in extremely high yields, e.g., in excess of 90%.

In a preferred embodiment, the 6-amino-4(3H)-X-pyrimidine of Formula III is 2,6-diamino-4(3H)-X-pyrimidine and the nitroolefin of Formula IV is a 1-nitrobut-1-ene or 1-nitropent-1-ene further substituted with a cyclic structure:

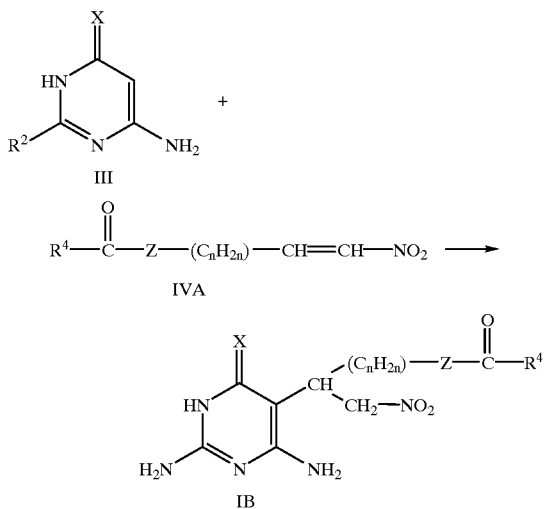

As above, $R^4$ is a carboxylic acid protecting group, Z is phenylene, thienediyl, or furandiyl, and n has a value of 0 to 4, notably 2 or 3. Z preferably is 1,3-phenylene, 1,4-phenylene, thiene-2,4-diyl, thiene-2,5-diyl, thiene-3,4-diyl, or thiene-3,5-diyl, most preferably 1,4-phenylene.

$R^4$ as a carboxylic acid protecting group can be an ester group that is selectively removable under sufficiently mild conditions not to disrupt the desired structure of the molecule, especially a lower alkyl ester of 1 to 12 carbon atoms such as methyl or ethyl. As described above, the reactions effected with compounds of Formula IVA are such that simple alkyl esters are hydrolyzed and thus serve admirably as carboxylic acid protecting groups. Alkyl groups that are branched at the 1-position such as tert.-butyl also are useful, as are lower alkyl esters substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)methyl; or (v) aroyl, such as phenacyl. A carboxy group also can be protected in the form of an organic silyl group such as tri-lower alkylsilyl, as for example tri-methylsilyloxycarbonyl.

In the preferred 1-nitroalk-1-enes of Formula IVA, n has a value of 0 to 4, notably 2 or 3, Z is phenylene, thienediyl, or furandiyl, and $R^4$ is a carboxylic acid protecting group. A preferred protecting group for $R^4$ on the basis of cost and availability is alkoxy of 1 to 6 carbon atoms, particularly 1 to 4 carbon atoms. The numbering of the 1-nitroalk-1-enes of Formula IV will depend upon the manner in which the compound is named. Thus a 1-nitrobut-1-ene substituted with a phenyl group which in turn is substituted in the para-position with carbomethoxy would preferably be named as a methyl benzoate derivative, specifically methyl 4-(4-nitrobut-3-en-1-yl)benzoate, methyl 4-(5-nitropent-4-en-1-yl)benzoate. Other typical compounds include methyl 4-(5-nitropent-4-en-2-yl)benzoate, ethyl 4-(4-nitrobut-3-en-1-yl)benzoate, ethyl 4-(5-nitropent-4-en-4-yl)benzoate, ethyl 4-(5-nitropent-4-en-2-yl)benzoate, t-butyl 4-(4-nitrobut-3-en-1-yl)benzoate, t-butyl 4-(5-nitropent-4-en-4-yl)benzoate, t-butyl 4-(5-nitropent-4-en-2-yl)benzoate, methyl 5-(4-nitrobut-3-en-1-yl)thiene-2-carboxylate, methyl 5-(5-nitropent-4-en-1-yl)thiene-2-carboxylate, methyl 5-(5-nitropent-4-en-2-yl)thiene-2-carboxylate, methyl 4-(4-nitrobut-3-en-1-yl)thiene-2-carboxylate, ethyl 4-(5-nitropent-4-en-1-yl)thiene-2-carboxylate, methyl 4-(5-nitropent-4-en-2-yl)thiene-2-carboxylate, ethyl 5-(4-nitrobut-3-en-1-yl)thiene-3-carboxylate, methyl 5-(5-nitropent-4-en-1-yl)thiene-3-carboxylate, ethyl 5-(5-nitropent-4-en-2-yl)thiene-3-carboxylate, methyl 4-(4-nitrobut-3-en-1-yl)thiene-3-carboxylate, ethyl 4-(5-nitropent-4-en-1-yl)-thiene-3-carboxylate, methyl 4-(5-nitropent-4-en-2-yl)thiene-3-carboxylate, β-nitrostyrene, methyl 4-(2-nitrovinyl)benzoate, diethyl N-[4-(4-nitrobut-3-en-1 -yl)benzoyl]glutamate, diethyl N-[4-(5-nitropent-4-en-1-yl)benzoyl]glutamate, and the like.

The preferred compounds of Formula III are 2,6-diamino-4(3H)-oxopyrimidine and 2,4,6-triaminopyrimidine.

According to a third embodiment, the two foregoing transformations are combined and a 6-amino-4(3H)-X-pyrimidine is treated in an inert solvent with a unsubstituted or substituted 1-nitroalk-1-ene to yield a 5-substituted-6-amino-4(3H)-X-pyrimidine in which the 5-position substituent is a 1-nitroalk-2-yl group. This 5-substituted 6-amino-4 (3H)-X-pyrimidine intermediate is then converted to the aldehyde and the element of water removed to form the corresponding 5-substituted 4(3H)-X-7H-pyrrolo[2,3-d] pyrimidine, as for example through sequential treatment with (a) dilute aqueous base at ambient temperatures and (b) aqueous acid at reduced temperatures.

The present process thus provides a direct and inexpensive route to 5-substituted 4(3H)-X-7H-pyrrolo[2,3-d] pyrimidines starting with a 6-amino-4(3H)-X—pyrimidine, utilizing a nitroolefin as the only other constitutive reactant, and involving only two isolation steps:

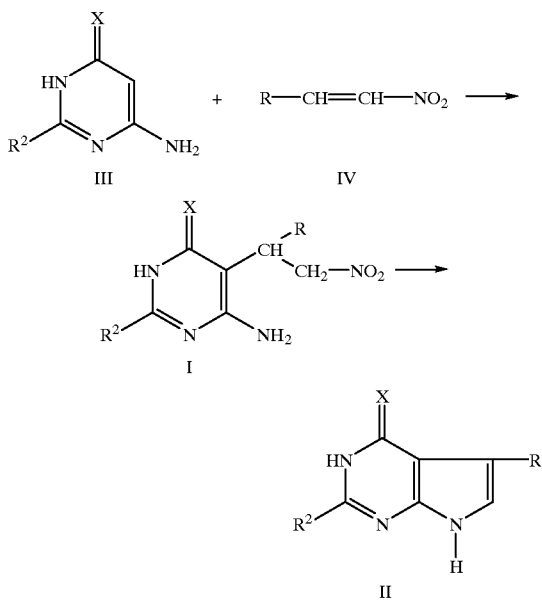

The 1-nitroolefin of Formula IV can be readily obtained through conventional methods. For example, an unsubstituted or substituted alkyl or aryl aldehyde can be treated with nitromethane to form the corresponding 1-nitroalkan-2-ol of one more carbon atom that, in turn, is dehydrated, as for example with methanesulfonyl chloride followed by triethylamine. In this manner, for example, benzaldehyde and nitromethane are allowed to react to yield 2-nitro-1-hydroxyethylbenzene which is dehydrated to yield β-nitrostyrene

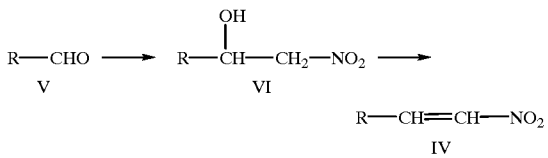

The following examples will serve to further typify the nature of the invention but should not be construed as a limitation on the scope thereof which is defined solely by the appended claims. The disclosures of all noted references are incorporated herein by reference.

EXAMPLE 1

1-Nitro-2-(2,6-diamino-4(3H)-oxopyrimidin-5-yl)-4-(4-ethoxycarbonylphenyl)butane A mixture of 1.41 g (5.7 mmol) of 1-nitro-4-(4-ethoxycarbonylphenyl)-1-butene and 0.72 g (5.7 mmol) of 2,6-diamino-4(3H)oxopyrimidine in 20 mL of water and 20 mL of ethyl acetate was stirred at 50° C. for 24 hours. The solid slowly disappeared. The reaction mixture was poured into 200 mL of ethyl acetate, washed with water (2×40 mL), dried over anhydrous sodium sulfate, and then concentrated under reduced pressure. The residue was purified by column chromatography on silica gel, eluting with 8:1 ethyl acetate:methanol, to afford 1.95 g (91%) of 1-nitro-2-(2,6-diamino-4(3H)-oxopyrimidin-5-yl)-4-(4-ethoxycarbonylphenyl)-butane as a light yellow solid: IR (KBr) 3461, 3368, 3198, 2922, 1704, 1611, 1545, 1436, 1375,1281, 1177, 1101,1013, 784, 761 cm$^{-1}$. $^1$H NMR (DMSO-d6) δ 9.84 (1H, rb s), 7.83 (2H, d, J=8.0 Hz), 7.25 (2H, d, J=8.0 Hz), 6.09 (2H, br s), 5.97 (2H, br s), 5.00 (1H, t, J=10.0 Hz), 4.76 (1H, dd, J=12.0 and 6.5 Hz), 4.27 (2H, q, J=7.0 Hz), 3,39 (1H, m), 2.65 (1H, td, J=11.5 and 5.5 Hz), 2.50 (1H, td, J=11.5 and 5.0 Hz), 2.17–2.09 (1H, m), 1.70(1H, m), 1.29(3H, t, J=7.0 Hz); $^{13}$C NMR (DMSO-d$_6$) δ 165.71, 162.64, 161.89, 153.53, 148.15, 129.20, 128.39, 127.37, 83.89, 77.59, 60.49, 34.99, 32.59, 31.28, 14.19. EIMS m/z 375 (M+), 357, 240, 328, 283, 202,180,163,151, 145, 136,109, 98, 90, 77, 68.

EXAMPLE 2

4-[2-(2-Amino-4(3H)-oxo-7H-pyrrolo[2,3-d]pyrimidin-5-yl)ethyl]benzoic Acid

To a mixture of 0.24 g (6.0 mmol) of sodium hydroxide in 3.0 mL of water was added 0.375 g (1.0 mmol) of 1-nitro-2-(2,6-diamino-4(3H)-oxopyrimidin-5-yl)-4-(4-ethoxycarbonylphenyl)butane at room temperature. The mixture was stirred at room temperature for 2 hours and then was slowly added to 0.98 g (10.0 mmol) of sulfuric acid in 4.0 mL of water at 0° C. After 3 hours, the pH was adjusted to 7 by the addition of base (2.0 N aqueous sodium hydroxide). The mixture was stirred at room temperature for another hour and the mixture then acidified by the addition of acetic acid (0.5 mL). The precipitated solid was collected by filtration, washed with water followed by ethyl acetate, and dried under vacuum to give 0.17 g (57%) of 4-[2-(2-amino-4(3H)-oxo-7H-pyrrolo[2,3-d]pyrimidin-5-yl)ethyl] benzoic acid as a light green solid which was >98% pure as indicated by $^1$H NMR. It was used without further purification for the next reaction: IR (KBr) 3467, 3328, 3198, 2919, 1645, 1536, 1431, 1381, 1273, 1172, 1072, 839, 779, 759 cm$^{-1}$, $^1$H NMR (DMSO-d$_6$) δ 10.61 (1H, s), 10.16 (1H, s), 7.83 (2H, d, J=8.0 Hz), 7.31 (2H, d, J=7.5 Hz), 6.31 (1H, s), 6.00 (2H, br s), 2.98 (2H, t, J=8.0 Hz), 2.85 (2H, t, J=8.0 Hz); $^{13}$C NMR (DMSO-d$_6$) δ 127.29, 159.04, 152.02, 150.08, 147.75, 129.21, 128.44, 128.18, 117.69, 113.59, 98.74, 36.21, 27.77, EIMS m/z 298 (M+), 210, 170, 169, 163, 151, 142, 139, 126, 105,91, 77, 69.

The product of this example is a known chemical intermediate, the conversion of which to the known antineoplastic agent N-[4-{2-(2-amino-4(3H)-oxo-7H-pyrrolo[2,3-d]pyrimidin-5-yl)ethyl}benzoyl]-L-glutamic acid is typified in Example 3.

EXAMPLE 3

N-[4-{2-(2-Amino-4(3H)-oxo-7H-pyrrolo[2,3-d]pyrimidin-5-yl)ethyl}benzoyl]-L-glutamic acid A. Diethyl N-[4-{2-(2-Amino-4(3H)-oxo-7-H-pyrrolo[2,3-d]pyrimidin-5-yl)ethyl}-benzoyl]-L-glutamate To a suspension of 185 mg (0.62 mmol) of 4-[2-(2-amino-4(3H)-oxo-7H-pyrrolo[2,3-d]pyrimidin-5-yl)ethyl]benzoic acid in 15 mL of dry dimethyl formamide were added 0.08 mL (0.74 mmol) of 4-methylmorpholine and 130 mg (0.74 mmol) of 2-chloro-4,6-dimethoxy-1,3,5-triazine. The resulting mixture was stirred at room temperature for 2 hours, an additional 0.08 mL of 4-methylmorpholine and 221 mg (0.93 mmol) of diethyl L-glutamate hydrochloride were added, and the reaction mixture was stirred for 3.5 hours at room temperature. The solvent was evaporated under reduced pressure and the residue was purified by column chromatography on silica gel, eluting with 9:1 ethyl acetate:methanol, to give 186 mg (62%) of diethyl N-[4-{2-

(2-amino-4(3H)-oxo-7-H-pyrrolo[2,3-d]pyrimidin-5-yl)ethyl}-benzoyl]-L-glutamate as an off-white solid: IR (KBr) 3340, 3216, 2979, 1728, 1635, 1538, 1499, 1437, 1371, 1204, 1095, 1021, 785, 668 cm$^{-1}$, $^1$H NMR (DMSO-d$_6$) δ 10.64 (1H, s), 10.21 (1H, s), 8.64 (1H, d, J=5.0 Hz), 7.79 (2H, d, J=7.5 Hz), 7.30 (2H, d, J=8.0 Hz), 6.32 (1H, s), 6.07 (2H, br s), 4.44 (1H, q, J=5.0 Hz), 4.11 (2H, q, J=7.0 Hz), 4.05 (2H, q, J=7.0 Hz), 2.99 (2H, t, J=8.0 Hz), 2.87 (2H, t, J=8.0 Hz), 2.44 (2H, t, J=7.5 Hz), 2.15–2.08 (1H, m), 2.05–1.97 (1H, m), 1.19 (3H, t, J=6.5 Hz), 1.17 (3H, t, J=6.5 Hz); $^{13}$C NMR (DMSO-d$_6$) δ 172.24, 171.86, 166.68, 159.25, 152.18, 151.02, 146.31, 131.11, 128.19, 127.42, 117.66, 113.48, 98.75, 60.54, 59.93, 51.98, 36.14, 30.19, 27.99, 25.71, 14.07 (two carbons); EIMS m/z 483 (M+), 321, 281, 252, 191, 163, 141, 129, 119, 100, 91, 84; HRMS calc+d for C$_{24}$H$_{29}$N$_5$O$_6$483.2118, found 483.2119.

B. N-[4-{2-(2-Amino-4(3H)-oxo-7H-pyrrolo[2,3-d]pyrimidin-5-yl)ethyl}benzoyl]-L-glutamic acid To a solution of 80 mg (0.166 mmol) of diethyl N-[4-{2-(2-amino-4(3H)-oxo-7H-pyrrolo[2,3-d]pyrimidin-5-yl)ethyl}benzoyl]-L-glutamate in 3.0 mL of tetrahydrofuran was added 1.0 mL of 1 N aqueous sodium hydroxide at room temperature. The resulting mixture was stirred for 3.5 hours. The tetrahydrofuran was removed by evaporation under reduced pressure and the resulting mixture was acidified with acetic acid. The precipitate that separated was collected by filtration, washed with water (3×10 mL) followed by ethyl acetate (3×10 mL), and dried under vacuum to afford 52 mg (73%) of N-[4-{2-(2-amino-4(3H)-oxo-7H-pyrrolo[2,3-d]pyrimidin-5-yl)ethyl}benzoyl]-L-glutamic acid as an off-white solid: $^1$H NMR (DMSO-d$_6$) δ 12.48 (2H, s), 10.60 (1H, s), 10.51 (1H, 5), 8.48 (1H, d, J=7.0 Hz), 7.78 (2H, d, J=7.5 Hz), 7.29 (2H, d, J=7.5 Hz), 6.30 (1H, s), 6.00 (2H, br 5), 4.38 (1H, q, J=4.5 Hz), 2.97 (2H, t, J=7.0 Hz), 2.85 (2H, t, J=7.0 Hz), 2.35 (2H, t, J=7.0 Hz), 2.12–2.02 (1H, m), 1.97–1.92 (1H, m); $^{13}$C NMR (DMSO-d6) δ 173.87, 173.47, 166.51, 159.25, 152.18, 151.02, 146.17, 131.29, 128.15, 127.37, 117.63, 113.44, 98.72, 51.86, 36.14, 30.40, 21.02, 25.90; EIMS m/z 428 (MH+).

N-[4-{2-(2-Amino-4(3H)-oxo-7H-pyrrolo[2,3-d]pyrimidin-5-yl)ethyl}benzoyl]-L-glutamic acid exhibits activity against TS, DHFR, glycinamide ribonucleotide formyltransferase (GAR FTase), aminoimidazolecarboxamide ribonucleotide formyltransferase (AICAR TFase), and both domains of the C-I tetrahydrofolate synthetase enzyme {Taylor et al., *J Med. Chem.*, 35, 4450 (1992); Shih et al., *Cancer Research*, 57, 1116 (1997)}.

EXAMPLE 4

1-Nitro-4-(4-ethoxycarbonylphenyl)-1-butene

The preparation of the starting material in Example 1, 1-nitro-4-(4-ethoxycarbonylphenyl)-1-butene, can be exemplified as follows:

A. 3-(4-Ethoxycarbonylphenyl)-1-propanal

To a solution of 20 g (69.9 mmol) of ethyl 4-iodobenzoate, 0.47 g (2.1 mmol) of palladium acetate, 14.7 g (175 mmol) of sodium bicarbonate, and 22.5 g (70 mmol) of tetrabutylammonium bromide in 200 mL of dimethyl formamide were added, under nitrogen, 6.89 g (118.8 mmol) of allyl alcohol. The reaction mixture was stirred at room temperature for 42 hours. The dimethyl formamide was then removed by evaporation under reduced pressure and the residue was dissolved in 300 mL of ethyl acetate. This was washed with water (3×50 mL), dried over anhydrous sodium sulfate, and concentrated under reduced pressure. The residual solid was purified by column chromatography on silica gel, eluting with 7:3 hexane:ethyl acetate to give 13.3 g (98%) of 3-(4-ethoxycarbonylphenyl)-1-propanal as a light yellow oil. $^1$H NMR (CDCl$_3$) δ 10.02 (1H, s), 8.18 (2H, d, J=7.3 Hz), 7 47 (2H, d, J=7.3 Hz), 4.56 (2H, q, J=6.5 Hz), 3,21 (2H, t, J=6.5 Hz), 3.02 (2H, t, J=6.5 Hz), 1,59 (3H, t, J=6.5 Hz), Taylor, E. C. et al., *J. Org. Chem.*, 57, 3218 (1992); *J. Org. Chem.*, 60, 6684 (1995).

B. 1-Nitro-4-(4-Ethoxycarbonylphenyl)-2-butanol

To a stirred mixture of 2.25 (37 mmol) of nitromethane, 1.2 mL of ethanol and 0.06 mL of 10N aqueous sodium hydroxide solution was added 7.18 g (37 mmol) of 3-(4-ethoxycarbonylphenyl)-1-propanal at room temperature. After addition of the aldehyde, 0.06 mL of 10N aqueous sodium hydroxide and 0.23 mL of ethanol were added, and the resulting mixture was stirred at 38° C. for 48 hours and then poured into a mixture of ethyl acetate (100 mL) and hexanes (100 mL). The resulting solution was washed with water (2×20 mL), dried over anhydrous sodium sulfate and concentrated under reduced pressure. The residual solid was purified by column chromatography on silica gel, eluting with 1:4 ethyl acetate:hexanes, to afford 4.1 g (72%) of 1-nitro-4-(4-ethoxycarbonylphenyl)-2-butanol as a white solid, IR (KBr) 3439, 2929, 1700, 1619, 1553, 1362, 1289, 1180, 1137, 1105, 1019, 882, 739 cm$^{-1}$. $^1$H NMR (CDCl$_3$) δ 7.98 (2H, d, J=8.5 Hz), 7.28 (2H, d, J=8.0 Hz), 4.42 (2H, d, J=5.5 Hz), 4.38 (2H, q, J=7.0 Hz), 4.34–4.29 (1H, m), 3.03 (1H, br s), 2.96–2.90 (1H, m), 2.84–2.78 (1H, m), 1.92–1.78 (2H, m), 1.40 (3H, t, J=7.0 Hz); $^{13}$C NMR (CDCl$_3$) 8166.86, 146.36, 130.05, 128.70, 128.61, 80.76, 67.85, 61.15, 34.99, 31.50, 14.46; EIMS m/z 267 (M+), 265, 252, 249, 232, 222, 206, 177, 161, 149, 133, 105, 91, 77; HRMS calc'd for C$_{13}$H$_{17}$NO$_5$267.1107, found 267.1095.

C. 1-Nitro-4-(4-ethoxycarbonylphenyl)-1-butene

To a solution of 4.89 g (18.1 mmol) of 1-nitro-4-(4-ethoxycarbonylphenyl)-2-butanol in 24 mL of dry methylene chloride at 0° C. was added 2.1 g (18.1 mmol) of methanesulfonyl chloride followed by addition of 3.66 g (36.2 mmol) of triethylamine. The mixture was stirred at 0° C. for 20 minutes, poured into 40 mL of water, extracted with 50 mL of methylene chloride, dried over anhydrous, and concentrated under reduced pressure. The residual solid was purified by column chromatography on silica gel, eluting with 1:9 ethyl acetate:hexanes, to afford 4.1 g (90%) of 1-nitro-4-(4-ethoxycarbonylphenyl)-1-butene as a light yellow solid: IR (KBr) 3112, 2982, 1713, 1647, 1610, 1519, 1424, 1417, 1353, 1277, 1178, 1104, 1021, 954, 935, 857, 766, 706 cm$^{-1}$. $^1$H NMR (CDCl$_3$) δ 8.02 (2H, d, J=8.5 Hz), 7.28 (1H, dt, J=14.0 and 7.5 Hz), 7.27 (2H, d, J=8.5 Hz), 6.98 (1H, d, J=14.0 Hz), 4.39 (2H, q, J=7.0 Hz), 2.92 (2H, t, J=7.5 Hz), 2.64 (2H, q, J=8.0 Hz), 1.42 (3H, t, J=7.0 Hz); $^{13}$C NMR (CDCl$_3$) δ 166.55, 144.90, 140.91, 140.39, 130.23, 129.27, 128.49, 61.16, 34.12, 29.89, 14.52; EIMS m/z 249 (M+), 204, 202, 163, 135, 129, 118, 107, 90, 77; HRMS calc'd for C$_{13}$H$_{15}$NO$_4$ 249.1001 found 249.1029.

EXAMPLE 5

1- Nitro-2-(2,6-diamino-4(3H)-oxopyrimidin-5-yl)-5-(4-methoxycarbonylphenyl)pentane Following the procedure of Example 1, 1-nitro-2-(2,6-diamino-4(3H)-oxopyrimidin-5-yl)-5-(4-methoxycarbonylphenyl)pentane was obtained in 85% yield from 1-nitro-5-(4-methoxycarbonylphenyl)-1-pentene as a light yellow solid: IR (KBr) 3483, 3374, 3196, 2947, 1708, 1622,1541,1428, 1377,1277, 1179, 1110, 791, 760 cm$^{-1}$; $^1$H NMR (CDCl$_3$) δ 1.34–1.43 (1H, m), 1.44–1.62 (2H, m), 1. 82–1.94 (1 H, m), 2.47–2.67 (2H, m), 3.25–3.43 (1H, br s), 3.82 (3H, s), 4.71 (1H, dd, J=12.0 and 6.5 Hz), 4.97 (1H, br t), 5.93 (2H, br s), 6.03 (2H, br s), 7.29 (2H, d, J=8.0 Hz), 7.84 (2H, d, J=8.0 Hz), 9.77 (1H, s); $^{13}$C NMR (CDCl$_3$) δ 166.21, 162.76, 161.86, 153.48, 148.31, 129.17, 128.62, 127.11, 84.15, 77.76, 51.93, 35.15, 34.67, 29.21, 28.40; EIMS m/z 375 (M+), 341, 328, 297, 218. 190, 180, 164, 151, 126, 109, 99, 91, 77, 68; HRMS calcd for C$_{17}$H$_{21}$NO$_5$O$_5$ 375.1542, found 375.1559.

EXAMPLE 6

4-[3-(2-Amino-4(3H)-oxo-7H-pyrrolo[2,3-d]pyrimidin-5-yl)propyl]-benzoic Acid From 257 mg (0.66 mmol) of 1-nitro-2-(2,6-diamino-4(3H)-oxopyrimidin-5-yl)-5-(4-methoxycarbonylphenyl) pentane there was obtained, under the conditions of Example 2, 107 mg (50.7%) of product as a light blue solid that was used in for coupling without further purification: IR (KBr) 3490, 3375, 2950, 1700, 1657, 1544, 1428, 1276, 1180, 780 766 cm$^{-1}$; $^1$H NMR (DMSO-d6) δ 1.92 (2H. quintet, J=7.5 Hz), 2.58 (2H, t, J=7.5 Hz), 2.65 (2H, t, J=7.5 Hz), 6.15 (2H, br s), 6.39 (1H, s), 7.31 (2H, d, J=8.0 Hz), 7.84 (2H, d, J=8.0 Hz), 10.25 (1H, s), 10.71 (1H, s), EIMS n/z 312 (M+), 252, 207, 190, 170, 164, 150, 135, 126, 119, 107, 105, 98, 78, 64; HRMS calc'd for C$_{16}$H$_{16}$N$_4$O$_3$ 312.1222, found 312.1242.

EXAMPLE 7

N-[4-{3-(2-Amino-4(3H)-oxo-7H-pyrrolo[2,3-d]pyrimidin-5-yl)propyl}benzoyl]-L-glutamic Acid A. Diethyl N-[4{3-(2-Amino-4(3H)-oxo-7H-pyrrolo[2,3-d]pyrimidin-5-yl)propyl}benzoyl]-L-glutamate Following the procedure of Example 3A, diethyl N-[4{-3-(2-amino-4(3H)-oxo-7H-pyrrolo[2,3-d]pyrimidin-5-yl)propyl}benzoyl] L-glutamate was obtained from 4-[3-(2-amino-4(3H)-oxo-7H-pyrrolo[2,3-d]pyrimidin-5-yl)propyl]-benzoic acid in 51% yield as an off-white solid, m.p. 56–58° C.; $^1$H NMR (HDCl$_3$) δ 1.19 (3H, t, J=7.0 Hz), 1.29 (3H, t, J=7.0 Hz), 1.92-2-02 (2H, m), 2.122.20 (1H, m), 2.24–2.32 (1H, m), 2.40–2.54 (2H, m), 2.61 (2H, t, J=7.0 Hz), 2.68 (2H, t, J=7.0 Hz), 4.04–4-11 (2H, m), 4.23 (2H, t, J=7.0 Hz), 4.84 (1H, q, I=7.0 Hz), 5.37 (2 H, br s), 6.38 (1H, s), 7.18 (2H, d, J=8.0 Hz), 7.67 (2H, d, J=8.0 Hz), 7.74 (1 H, d, J=7.5 Hz), 9.33 (1H, s), 10.96 (1H, s).

B. N-[4-{3-(2-Amino-4(3H)-oxo-7H-pyrrolo[2,3-d]pyrimidin-5-yl)propyl}benzoyl]-L-glutamic Acid By following the procedure of Example 3B, N-[4-{3-(2-amino-4(3H)-oxo-7H-pyrrolo[2,3-d]pyrimidin-5-yl)propyl}benzoyl]-L-glutamic acid was isolated in 68% yield from diethyl N-[4-{3-(2-amino-4(3H)-oxo-7H-pyrrolo[2,3-d]pyrimidin-5-yl)propyl}benzoyl] L-glutamate as an off-white solid; IR (KBr) 3289, 2929, 1693, 1651, 1541, 1502, 1400, 1337, 1302, 1236, 1109, 1095, 765, 680 cm$^{-1}$; $^1$H NMR (DMSO-d6) δ 1.92 (2H, quintet, J=7.0 Hz), 1.94–1.98 (1H, m), 2.02–2.12 (1H, m), 2.34 (2H, t, J=7.0 Hz), 2.58 (2H, t, J=8.0 Hz), 2.64 (2H, i, J=7.5 Hz), 4.38 (1H, q, J=5.0 Hz), 5.97 (2H, s), 6.36 (1H, s), 7.29 (2H, d, J=8.0 Hz), 7.79 (2H, d, J=8.0 Hz), 8.48 (1H, d, J=7.5 Hz), 10.10 (1H, s), 10.63 (1H, s); EIMS m/z 442 (MH+).

EXAMPLE 8

1- Nitro-2-(2,4,6-triaminooxopyrimidin-5-yl)-5-(4-methoxycarbonylphenyl)pentane 1- Nitro-2-(2,4,6-triaminooxopyrimidin-5-yl)-5-(4-methoxycarbonylphenyl)pentane was isolated in 91% yield from 1-nitro-5-(4-methoxycarbonylphenyl)-1-pentene and 2,4,6-triaminopyrimidine according to the procedure of Example 1 as a light yellow solid: IR (KBr) 3481, 3394, 3184, 2949, 1709, 1613, 1569, 1437, 1286, 1180, 1114, 801, 766 cm$^{-1}$; $^1$H NMR (DMSO-d6) δ 1.44–1.64 (3H, m), 1.76–1.84 (1H, m), 2.63 (2H, q, J=6.5 Hz), 3.55 (1H, m), 3.82 (3H, s), 4.81 (2 H, m), 5.38 (2H, s), 5.60 (2H, br s), 5.70 (2H, br s), 7.30 (2H, d, J=8.0 Hz), 7.86 (2H, d, J=8.5 Hz); $^{13}$C NMR (DMSO-d6) 166–21, 163.42, 161.25, 160.79, 148.09, 129.22, 128.62, 127.16, 82.07, 77.16, 51.95, 35.02, 33.80, 28–68, 28.49; EIMS m/z 376(M$^{+2+}$), 374 (M$^+$), 366, 258, 342, 328, 314, 232, 218, 202, 187, 163, 149,140,132, 125, 98, 92, 85, 77, 67.

EXAMPLE 9

4-[3-(2,4-Diamino-7H-pyrrolo[2,3-d]pyrimidin-5-yl)propyl]benzoic Acid

From 300 mg (0.80 mmol) of 1-nitro-2-(2,4,6-triaminopyriniidin-5-yl)-5-(4-methoxycarbonylphenyl) pentane there was obtained, under the conditions of Example 2, 110 mg (44%) of 4-[3-(2,4-diamino-7H-pyrrolo[2,3-d]pyrimidin-5-yl)propyl]benzoic acid (See, e.g., Taylor et al., *J. Org. Chem.*, 1996, 61, 7973; Miwa et al., *J. Med. Chem.*, 1991, 34, 555) as a white solid: IR (KBr) 3334, 3202, 2931, 1645, 1549, 1328, 1272, 1111, 780, 620 cm$^{-1}$; $^1$H NMR (DMSO-d6) 6 1.84 (2H, quintet, J=7.5 Hz), 2.69 (2H, t. J=7.5 Hz), 2.71 (2H, t, J=7.5 Hz), 5.80 (2H, br s), 6.38 (2H, br s), 6.50 (1H, s), 7.32 (2H, d, J=8.0 Hz), 7.85 (2H, d, J=8.0 Hz), 10.66 (1H, s), 11.61 (1H, br s); EIMS m/z 311 (M$^+$), 229, 183, 163, 151, 140,125, 109, 91, 78.

EXAMPLE 10

1-Nitro-5-(4-methoxycarbonylphenyl)-1-pentene

The preparation of the starting material in Example 5, 1-nitro-5-(4-methoxycarbonylphenyl)-1-pentene, can be exemplified as follows:

A. 4-(4-Methoxycarbonylphenyl)butyraldehyde

A Parr flask was charged with 3.25 g (15.98 mmol) of methyl 4-(4-hydroxy-1-butynyl)benzoate (Taylor et al. *J. Org. Chem.*, 1990, 55, 3222–3227) and 0.26 g (8% wt equivalent) of 10% palladium-on-carbon catalyst in 40 mL of ethanol. Hydrogenation was carried out at 50 psi of hydrogen for 18 hours. The mixture was filtered through a silica gel pad that was subsequently washed with ethanol. The combined filtrates were concentrated under reduced pressure to give 3.20 g (97%) of methyl 4-(4-hydroxybutyl) benzoate as a light yellow oil. $^1$H NMR (CDCl$_3$) δ 1.51 (1H, s), 1.57–1.82 (4H, m), 2.74 (2H, t, J=7.3 Hz), 3.71 (2H, t, J=6.0 Hz), 3.94 (3H, s), 7.27 (2H, d, J=8.0 Hz), 7.99 (2H, d, J=8.0 Hz).

To a mixture of 4.97 g (23 mmol) of pyridinium chlorochromate and 1.23 g (15 mmol) of sodium acetate in 100 mL of dry methylene chloride was added 3.2 g (15.3 mmol) of methyl 4-(4-hydroxybutyl)benzoate in 50 mL of methylene chloride at room temperature. The resulting mixture was stirred at room temperature for 3 hours, diluted with 150 mL of ethyl ether, filtered through a silica gel pad, and concentrated. The residue was purified by column chromatography (silica gel/hexane:ethyl acetate=4:1) to give 2.85 g (90%) of 4-(4-methoxycarbonylphenyl)butyraldehyde as a light yellow oil: $^1$H NMR (CDCl$_3$) δ 2.15–2.40 (2H, m), 2.72 (2H, t, J=6.6 Hz), 2.96 (2H, t, J=7.2 Hz), 4.15 (3H, s), 7.50 (2H, d, J=8.1 Hz), 8.21 (2H, d, J=8.1 Hz), 10.01 (1H. s); MS m/z 206 (M$^+$), 175, 162, 131,103, 91, 63.

B. 1-Nitro-5-(4-methoxycarbonylphenyl)-2-pentanol

Following the procedure of Example 4B, 1-nitro-5-(4-methoxycarbonylphenyl)-2-pentanol was isolated in 61% yield as a light yellow solid: IR (KBr) 3503, 3025, 2944, 1701, 1557, 1289, 1102, 761, 699 cm$^{-1}$: $^1$H NMR (CDCl$_3$) δ 1.49–1.62 (2H, m), 1.70–1.79 (1H, m), 1.86–1.95 (1H, m), 2.73 (2H, t, J=8.0 Hz), 2.86 (1H, d, J=3.5 Hz), 3.92 (3H, s), 4.35–4.43 (3H, m), 7.25 (2H, d, J=8.0 Hz), 7.97 (2H, d, J=8.0 Hz). $^{13}$C NMR (CDCl$_3$) δ 167.33, 147.28, 129.97, 128.60, 128.19, 80.76, 68.56, 52.23, 35.60, 33.23, 26.75; EIMS m/z 267 (M$^+$), 249, 218, 206, 187, 175, 67.1104.

C. 1-Nitro-5-(4-methoxycarbonylphenyl)-1-pentene

Following the procedure of Example 4C, 1-nitro-5-(4-methoxycarbonylphenyl)-1-pentene was isolated in 96% yield as a light yellow oil: IR (neat) 3103, 1719, 1649, 1610, 1524, 1436, 1352, 1281, 1197, 1101, 1020, 962, 764 cm$^{-1}$; $^1$H NMR (CDCl$_3$) δ 1.90 (2H, quintet, J=8.0 Hz), 2.31 (2H, qd, J=7.5 and 1.5 Hz), 2.76 (2H, t. J=7.5 Hz), 3.93 (3H. s), 7.00 (1H, dt, J=13.5 and 1.5 Hz), 7.26 (2H, d, J=8.5 Hz), 7.29 (2H, dt, J=13.5 and 7.5 Hz), 8.00 (2H, d, J=8.5 Hz); $^{13}$C NMR (CDCl$_3$) δ 167.16, 146.49, 141.95, 140.14, 130.11, 128.61, 128.52, 52.25, 35.32, 29.13, 27.95; EIMS m/z 249 (M+), 232, 218, 202, 187, 171, 163, 149, 143, 131, 118, 103,91-77; HRMS calc'd for C$_{13}$H$_{15}$NO$_4$ 249.1001; found 249.0992.

EXAMPLE 11

1-Nitro-2-(2.6-diamino-4(3H)-oxopyrimidin-5-yl)-4-phenvlbutane

To a mixture of 1.85 g (10.5 mmol) of 1-nitro-4-phenyl-1-butene in a mixture of 20 mL of water and 20 mL of ethyl acetate at room temperature was added 1.16 g (9.0 mmol) of 2,6-diamino-4(3H)-oxopyrimidine. The resulting mixture was stirred for 18 hours, 100 mL of ethyl acetate added, and the organic layer separated, dried, and concentrated to afford a yellow solid that was washed with 2% ethyl acetate in hexane and dried to give 3.05 g (96%) of product as a yellow solid: IR (KBr) 3473, 3402, 2913,1622, 1537,1493, 1450, 1376, 1003, 781, 742, 696 cm$^{-1}$; $^1$H NMR (DMSO-d6) δ 1.66–1.73 (1H, m), 2.07–2.15 (1H, m), 2.47 (1 H, td, J=12.5 and 5.0 Hz), 2.58 (1H, td, J=13.0 and 5.0 Hz), 3.41 (1H, m), 4.77 (1H, dd, J=12.0 and 6.5 Hz), 5.03 (1H, t, J=10.0 Hz), 5.96 (2H, br s), 6.06 (2H, br s), 7.16–7.11 (3H, m), 7.25 (2H, t, J=7.0 Hz), 9.81 (1H, s); $^{13}$C NMR (CDCl$_3$) δ 162.85, 161.91, 153.54, 142.36, 128.25, 128.03, 125.57, 84.03, 77.65, 35.08, 32.98, 31.85; EIMS m/z 303 (M'), 268, 254, 242, 163, 151, 126, 109, 91, 77; HRMS calc'd for C$_{14}$H$_{17}$N$_5$O$_3$ 303.1331, found 303.1339.

EXAMPLE 12

2-Amino-4(3H)-oxo-5-phenyl-7H-pyrrolo[2.3-d]pyrimidine

To an aqueous solution of sodium hydroxide (34 g, 8.1 mmol, in 5 mL of water) was added 0.48 g (1.58 mmol) of 1-nitro-2-(2,6-diamino-4(3H)-oxo-pyrimidin-5-yl)-4-phenylbutane at room temperature. The mixture was stirred for 2 hours and then slowly added to an aqueous solution of 1.37 g (14 mmol) of 98% sulfuric acid in 5 mL of water at 0° C. The resulting mixture was stirred at 0° C. for one hour and then at room temperature for an additional hour. Concentrated aqueous ammonium hydroxide was added at 0° C. to adjust the pH to 7, and the precipitated solid was collected by filtration and purified by column chromatography (silica gel/ethyl acetate:methanol 9:1) to give 0.2 g (50%) of product as a light yellow solid, 2-amino-4(3H)-oxo-5-phenyl-7H-pyrrolo[2.3-d]pyrimidine, which as discussed above exhibits inhibitory activity against various enzymes (TS, DHFR, GAR Ftase, AICAR Tfase, etc.). IR (KBr) 3510, 3399, 3197, 2927, 1665, 1635, 1604, 1525, 1436, 1376, 783, 755, 701, 699 cm$^{-1}$; $^1$H NMR (DMSO-d6) δ 2.81-2-86 (2H, m), 2.87-2-93 (2H, m), 6.01 (2H, br s), 6.32 (1H, s), 7.15 (1H, t, J=7.0 Hz), 7.20 (2H, d, J=7.0 Hz), 7.25 (2H, t, J=7.0 Hz), 10.15 (1H, s), 10.61 (1H, s); 13C NMR (CDCl$_3$) δ 159.27, 152.15, 151.18, 142.46, 128.28, 128.10, 125–52, 117.99, 113.27, 98.75, 36.32, 28.31; EIMS m/z 254 (M+), 163, 146, 121, 91, 78, 69; HRMS calcd for C$_{14}$H$_{14}$N$_4$O 254.1168, found 254.1175.

EXAMPLE 13

1- Nitro-5-(4-methoxycarbonylphenyl)-1-pentene

The preparation of the starting material in Example 11, 1-nitro-4-phenyl-1-butene, can be exemplified as follows:

A. 1-Nitro-4:phenyl-2-butanol:

To a stirred mixture of 15 g (200 mmol, 14.4 mL) of nitromethane, 7.8 mL of ethanol and 0.39 mL of 10 N aqueous sodium hydroxide was added 26.8 g (200 mmol, 26.3 mL) of dihydrocinnamaldehyde at room temperature. After two-thirds of the aldehyde had been added, an additional 0.39 mL of 10 N aqueous sodium hydroxide and 1.5 mL of water and the remainder of the aldehyde were added. The resulting mixture was stirred at 38° C. for 65 hours, and the pH then adjusted to 7 by addition of 2 N hydrochloric acid. The yellow solid that separated was collected by filtration, washed with hexane, and dried in vacuo to give 35.0 g (90%) of product as a yellow solid: IR (KBr) 3375, 2952, 1558, 1445, 1385, 11961 1090, 878, 753, 704 cm$^{-1}$; $^1$H NMR (CDCl$_3$) δ 1,62–1.92 (2H, m), 2.54–3.00 (2H, m), 4.30 (1H, m), 4.32 (2H, d, J=9.0 Hz), 7.20–7.35 (5H, m); $^{13}$C NMR (CDCl$_3$) δ 140.77, 128.77, 128.55, 126.44, 80.73, 69–97, 35.29, 131.48; EIMS m/z 195 (M+), 177, 170, 160, 147, 133, 130, 115, 105, 91, 77.

B. 1-Nitro-4-phenyl-1-butene

To a solution of 5.85 g (30.0 mmol) of 1nitro-4-phenyl-2-butanol in 40 mL of dry methylene chloride at 0° C. was added 3.44 g (30.0 mmol) of methanesulfonyl chloride followed by addition of 6.07 g (60.0 mmol) of triethylamine. The mixture was stirred at 0° C. for 20 min, poured into 40 mL of water and extracted with 50 mL of methylene chloride. The extracts were dried over sodium sulfate, concentrated, and the residual solid purified by column chromatography (silica gel/ethyl acetate:hexanes 1:9) to afford 4.25 g (80%) of the product as a yellow oil. Since this material slowly decomposes at room temperature, it was used immediately for the next reaction: IR (neat) 3028, 2930, 1648, 1555, 1524, 1497, 1454, 1351, 1176, 953, 931, 750, 700 cm$^{-1}$; $^1$H NMR (CDCl$_3$) δ 2.63 (2H, q, J=7.0 Hz), 2.87 (2H, t, J=8.0 Hz), 7.00 (1H, dt, J=13.5 Hz), 7.21 (2H, d, J=7.5 Hz), 7.26–7.35 (4H, m); $^{13}$C NMR (CDCl$_3$) 5 141.55,140.18, 139.74, 128.90, 128.46, 126.81, 34.19, 30.29; EIMS m/z 177 (M+) 60, 143, 133, 130, 115, 103, 91, 77; HRMS calc'd for C$_{10}$H$_{11}$NO$_2$ 177.0790, found 177.0802.

EXAMPLE 14

1-Nitro-2-(2,6-diamino-4(3H)-oxopyrimidin-5-yl)-2-phenylethane

1-Nitro-2-(2,6-diamino-4(3H)-oxopyrimidin-5-yl)-2-phenylethane was obtained as a light yellow solid in 92% yield by employing 1-nitro-2-phenyethylene in the procedure of Example 1. IR (KBr) 3379, 3187, 2912, 1622, 1546, 1494, 1436, 1253, 793, 773 cm$^{-1}$; $^1$H NMR (DMSO-d6) δ 4.56 (1H, t, J=7.5 Hz), 5.30 (1H, dd, J=13.0 and 7.5 Hz), 5.46 (1H, dd, J=13.0 and 7.5 Hz), 6.12 (4H, s), 7.17 (1H, t, J=7.5 Hz), 7.25 (2H, t, J=7.5 Hz), 7.50 (2H, d, J=8.0 Hz), 9.90 (1H, s).

EXAMPLE 15

2-Amino-4(3H)-oxo-5-phenyl-7H-pyrrolo[2.3-d]pyrimidine

2-Amino-4-(3H)-oxo-5-phenyl-7H-pyrrolo[2.3-d] pyrimidine, which as discussed above exhibits inhibitory activity against various enzymes, was obtained in 20% yield as a dark-green solid from 1-nitro-2-(2,6-diamino-4(3H)-oxopyrimidin-5-yl)-2-phenylethane according to the procedure of Example 2: $^1$H NMR (DMSO-d6) δ 6.40 (2H, br s), 7.03 (1H, s), 7.12–7.56 (3H, m), 7.91 (2H, d, J=7.5 Hz), 10.58 (1H, brs), 11.33(1H, s).

EXAMPLE 16

1-Nitro-2-phenyethylene

The preparation of the starting material in Example 14, 1-nitro-4-phenyl-I -butene, can be exemplified as follows:
A. 2-Nitro-I-phenyl-I-ethanol 2-Nitro-I-phenyl-I-ethanol was obtained as a white solid in 88% yield from benzaldehyde and nitromethane according to the procedure of Example 4B. $^1$H NMR (CDCl$_3$) δ 3.10 (1H, br s), 4.53–4.70 (2H, m), 5.50 (1H, m), 7.30–7.55 (5H, m).
B. 1-Nitro-2-phenyethylene(β-Nitrostyrene)

1-Nitro-2-phenyethylene was obtained as a yellow solid in 85% yield from 2-nitro-I-phenyl-I-ethanol according to the procedure of Example 4C. $^1$H NMR (CDCl$_3$) δ 7.68–7.75 (3H, m), 7.75–7.81 (2H. m), 7.82 (1H, d, J=13.2 Hz), 8.24 (1H, d, J=13.2 Hz). $^{13}$C NMR (CDCl$_3$) δ139.14, 137.40, 132.29, 130.35, 129.60, 129.31.

What is claimed is:

1. Process for the preparation of a 4(3H)-X-7H-pyrrolo [2,3-d]pyrimidine in which X is =O or =NH which comprises (i) treating a 6-amino-4(3H)-X-pyrimidine in an inert solvent with a 1-nitroalk-1-ene which is unsubstituted or substituted in the 2-position to yield the corresponding 5-(1-nitroalk-2-yl)-6-amino-4(3H)-X-pyrimidime; (ii) converting said 5-(1-nitroalk-2-yl)-6-amino-4(3H)-X-pyrimidine to the corresponding 5-(1-oxoalk-2-yl)-6-amino-4(3H)-X-pyrimidine; and (iii) removing the elements of water from said 5-(1-oxoalk-2-yl)-6-amino-4(3H)-X-pyrimidine to effect cyclization and form said 4(3H)-X-7H-pyrrolo[2,3-d]pyrimidine.

2. The process according to claim 1 wherein said 1-nitroalk-1-ene contains more than 2-carbon atoms and said resultant 4(3H )-X-7H-pyrrolo[2,3-d]pyrimidine is substituted in the 5-position.

3. The process according to claim 2 wherein X is =O.
4. The process according to claim 2 wherein X is =NH.
5. The process according to claim 2 wherein said 1-nitroalk-1-ene is:

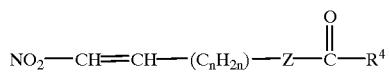

in which n has a value of 0 to 4,
Z is phenylene, thienediyl, or furandiyl, and
R$^4$ is a carboxylic acid protecting group.

6. The process according to claim 5 wherein said 6-amino-4(3H)-pyrimidine is 2,6-diamino-4-(3H)-oxopyrimidine.

7. The process according to claim 5 wherein said 6-amino-4(3H)-pyrimidine is 2,4,6-triaminopyrimidine.

8. The process according to claim 5 wherein n has a value of 2 or 3 and Z is 1,4-phenylene.

9. The process according to claim 8 wherein R$^4$ is alkoxy 1 to 6 carbon atoms.

10. The process according to claim 9 which comprises treating 2,6-diamino-4(3H)-X-pyrimidine, in which X is =O or =NH, with a 1-nitro-4-[4-(alkoxycarbonyl)phenyl] but-l-ene, in which the alkoxycarbonyl group contains from 1 to 4 carbon atoms, in an inert solvent to yield 1-nitro-2-(2,6-diamino-4(3H)-X-pyrimidin-5-yl)4-[4-(alkoxycarbonyl)phenyl]butane; (ii) treating said 1-nitro-2-(2,6-diamino-4(3H)-X-pyrimidin-5-yl)-4-[4-(lower alkoxycarbonyl)phenyl]butane with dilute aqueous base at ambient temperatures; and (iii) adding aqueous acid at reduced temperatures to form 4-[2-(2-amino-4(3H)-X-7H-pyrrolo[2,3-d]pyrimidin-5-yl)ethyl]benzoic acid.

11. The process according to claim 10 in which X is =O.

12. The process according to claim 9 which comprises treating 2,6-diamino-4(3H)-X-pyrimidine, in which X is =O or =NH, with a 1-nitro-5-[4-(alkoxycarbonyl)phenyl] pent-l-ene, in which the alkoxycarbonyl group contains from 1 to 4 carbon atoms, in an inert solvent to yield 1-nitro-2-(2,6-diamino-4(3H)-X-pyrimidin-5-yl)-5-[4-(alkoxycarbonyl)phenyl]pentane; (ii) treating said 1-nitro-2-(2,6-diamino-4(3H)-X-pyrimidin-5-yl)-5-[4-(lower alkoxycarbonyl)phenyl]pentane with dilute aqueous base at ambient temperatures; and (iii) adding aqueous acid at reduced temperatures to form 4-[3-(2-amino-4(3H)-X-7H-pyrrolo[2,3-d]pyrimidin-5-yl)propyl]benzoic acid.

13. The process according to claim 12 in which X is =NH.

14. Process for the preparation of a 4(3H)-X-7H-pyrrolo [2,3-d]pyrimidine in which X is =O or =NH which comprises (a) converting a 6-amino-4(3H)-X-pyrimidine substituted in the 5-position with an unsubstituted or substituted 1-nitroalk-2-yl group to the correspondingly 6-amino-4 (3H)-X-pyrimidine substituted in the 5-position with a 1-oxoalk-2-yl group, and (b) removing the elements of water from the resultant 5-(1 -oxoalk-2-yl)-6-amino-4(3H)-X-pyrimidine to form said 4(3H)-X-7H-pyrrolo[2,3-d] pyrimidine.

15. The process according to claim 14 wherein said 5-(1-nitroalk-2-yl)-6-amino-4(3H)-X-pyrimidine is converted to said 5-(1-oxoalk-2-yl)-6-amino-4(3H)-X-pyrimidine by treatment with dilute aqueous base at ambient temperatures.

16. The process according to claim 14 wherein said 4(3H)-X-7H-pyrrolo[2,3-d]pyrimidine is formed from said 5-(1-oxoalk-2-yl)-6-amino-4(3H)-X-pyrimidine by treatment with aqueous acid at reduced temperatures.

17. The process according to claim 8 wherein said 1-nitroalk-2-yl substituent is:

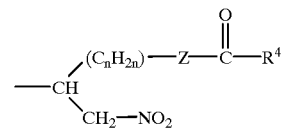

in which n has a value of 1 to 4,
Z is phenylene, thienediyl, or furandiyl, and
R$^4$ is a carboxylic acid protecting group.

18. The process according to claim 17 wherein n has a value of 2 or 3 and Z is 1,4-phenylene.

19. The process according to claim 18 wherein Z is alkoxy 1 to 6 carbon atoms.

20. The process according to claim 14 wherein said 6-amino-4(3H)-X-pyrimidine is 1-nitro-2-(2,6-diamino-4(3H)-oxopyrimidin-5-yl)-4-(4-carboxyphenyl)butane or 1-nitro-2-(2,6-diamino-4(3H)-oxopyrimidin-5-yl)-5-(4-carboxyphenyl)pentane in which the carboxylic acid group is protected as an alkyl ester of 1 to 6 carbon atoms.

21. The process according to claim 14 wherein said 6-amino-4(3H)-X-pyrimidine is 1-nitro-2-(2,4,6-triaminopyrimidin-5-yl)-4-(4-carboxyphenyl)butane or 1-nitro-2-(2,4,6-triaminopyrimidin-5-yl)-5-(4-carboxyphenyl)pentane in which the carboxylic acid group is protected as an alkyl ester of 1 to 6 carbon atoms.

22. A process for the preparation of a 6-amino-4(3H)-X-pyrimidine in which X is =O or =NH, which pyrimidine is substituted in the 5-position by an unsubstituted or substituted 1-nitroalk-2-yl group, which comprises treating a 6-amino-4(3H)-X-pyrimidine with the correspondingly unsubstituted or substituted 1-nitroalk-1-ene.

23. The process according to claim 22 wherein X is =O.

24. The process according to claim 22 wherein X is =NH.

25. The process according to claim 22 wherein said 1-nitroalk-1-ene is:

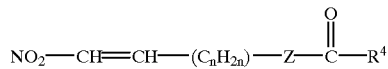

in which n has a value of 0 to 4,

Z is phenylene, thienediyl, or furandiyl, and $R^4$ is a carboxylic acid protecting group.

26. The process according to claim 25 wherein $R^4$ is alkoxy 1 to 6 carbon atoms.

27. The process according to claim 26 wherein n has a value of 2 or 3 and Z is 1,4-phenylene.

28. The process according to claim 26 wherein n has a value of 2 and X is =O.

29. The process according to claim 26 wherein n has a value of 3 and X is =NH.

* * * * *